(12) United States Patent
Liu

(10) Patent No.: US 10,732,435 B2
(45) Date of Patent: Aug. 4, 2020

(54) SMART CONTACT DEVICE

(71) Applicant: VERILY LIFE SCIENCES LLC, Mountain View, CA (US)

(72) Inventor: Zenghe Liu, Alameda, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 0 days.

(21) Appl. No.: 14/637,251

(22) Filed: Mar. 3, 2015

(65) Prior Publication Data

US 2016/0259180 A1    Sep. 8, 2016

(51) Int. Cl.
*G02C 7/04* (2006.01)
*G02C 11/00* (2006.01)

(52) U.S. Cl.
CPC .............. *G02C 7/04* (2013.01); *G02C 11/10* (2013.01)

(58) Field of Classification Search
CPC .......... G02C 7/022; G02C 7/028; G02C 7/04; G02C 11/10
USPC ........................................................ 351/158
See application file for complete search history.

(56) References Cited

U.S. PATENT DOCUMENTS

| | | | |
|---|---|---|---|
| 3,525,645 A * | 8/1970 | Duddy | H01M 12/04 429/406 |
| 6,120,460 A * | 9/2000 | Abreu | A61B 3/1241 600/405 |
| 7,655,193 B1 | 2/2010 | Rau et al. | |
| 7,947,239 B2 | 5/2011 | Lackner et al. | |
| 8,313,557 B2 | 11/2012 | Willauer et al. | |
| 8,337,589 B2 | 12/2012 | Wright et al. | |
| 8,742,623 B1 * | 6/2014 | Biederman | G02B 27/017 307/80 |
| 8,778,156 B2 | 7/2014 | Eisaman et al. | |

(Continued)

FOREIGN PATENT DOCUMENTS

| | | |
|---|---|---|
| EP | 1276795 | 3/2006 |
| EP | 2074066 | 7/2009 |

(Continued)

OTHER PUBLICATIONS

Eisaman, Matthew D., et al., "CO2 extraction from seawater using bipolar membrane electrodialysis", *Electronic Supplementary Material (ESI) for Environmental Science*, The Royal Society of Chemistry, (2012), 1-4.

(Continued)

*Primary Examiner* — Darryl J Collins
*Assistant Examiner* — Journey F Sumlar
(74) *Attorney, Agent, or Firm* — Christensen O'Connor Johnson Kindness PLLC (57) ABSTRACT

An eye contact device including at least one of a positive terminal including a first material having a standard reduction potential that is less than a standard reduction potential of chlorine; and a negative terminal including a second material having an electrode potential that favors reduction relative to a reduction of water. A method including one of forming a positive terminal of a two terminal device in an eye contact device, the positive terminal including a first material having a standard reduction potential that is less than a standard reduction potential of chlorine; and forming a negative terminal of the two terminal device including a second material having an electrode potential that favors reduction relative to a reduction of water.

19 Claims, 4 Drawing Sheets

(56) References Cited

U.S. PATENT DOCUMENTS

| | | |
|---|---|---|
| 8,784,632 B2 | 7/2014 | Eisaman et al. |
| 8,880,139 B1 | 11/2014 | Etzkorn et al. |
| 8,999,171 B2 | 4/2015 | Wallace et al. |
| 2008/0033338 A1 | 2/2008 | Smith |
| 2009/0001020 A1 | 1/2009 | Constantz et al. |
| 2010/0076553 A1 | 3/2010 | Pugh et al. |
| 2010/0233767 A1 | 9/2010 | McMurran |
| 2010/0288700 A1 | 11/2010 | Lahav et al. |
| 2011/0135551 A1 | 6/2011 | House et al. |
| 2011/0177550 A1 | 7/2011 | McMurran |
| 2011/0224578 A1 | 9/2011 | Edman et al. |
| 2012/0211421 A1 | 8/2012 | Self et al. |
| 2012/0220019 A1 | 8/2012 | Lackner et al. |
| 2012/0244053 A1 | 9/2012 | Self et al. |
| 2013/0008792 A1 | 1/2013 | Eisaman et al. |
| 2013/0034760 A1 | 2/2013 | Otts et al. |
| 2013/0343981 A1 | 12/2013 | Wright et al. |
| 2014/0000101 A1 | 1/2014 | Pugh et al. |
| 2014/0002788 A1* | 1/2014 | Otts .................. G02C 7/04 351/159.03 |
| 2014/0174929 A1* | 6/2014 | Luan ............ G01N 27/44791 204/543 |
| 2014/0272639 A1 | 9/2014 | Zietlow |
| 2014/0303452 A1 | 10/2014 | Ghaffari |
| 2014/0371565 A1* | 12/2014 | Glasser ............ A61N 1/36046 600/383 |

FOREIGN PATENT DOCUMENTS

| | | |
|---|---|---|
| EP | 2465600 | 6/2012 |
| EP | 2465601 | 6/2012 |
| EP | 2543427 | 1/2013 |
| WO | WO-9412465 | 6/1994 |
| WO | WO 00/25662 A1 | 5/2000 |
| WO | WO 2014/058647 A1 | 4/2014 |

OTHER PUBLICATIONS

Eisaman, Matthew D., et al., "CO2 separation using bipolar membrane electrodialysis", *Energy & Environmental Science*, vol. 4, No. 4, (Apr. 2011), 1319-1328.

PCT/US2016/017615—International Search Report & Written Opinion, dated May 4, 2016, 12 pages.

International Preliminary Report on Patentability mailed Mar. 3, 2015, for International Application No. PCT/US2016/017615, filed Feb. 11, 2016, 7 pages.

* cited by examiner

SMART CONTACT DEVICE

TECHNICAL FIELD

Optics and contact devices.

BACKGROUND INFORMATION

Smart eye contact devices or eye mountable devices that incorporate a processor and miniaturized technology offer unique opportunities for health monitoring and enhancement. Representative of the benefits of smart eye contact devices include the ability to diagnose and/or monitor disease states, provide drug delivery, employ reality augmentation, improve or adjust focus or accommodation and provide night vision.

Because a smart eye contact device or eye mountable device may include electronic devices such as an on-lens battery or rectifier, there is a potential hazard due to the wet environment in which the contact device is worn. More specifically, tears (e.g., basal tears) and/or water ingression at a two terminal device on a smart contact device offers the possibility of shorting of terminals and/or any metal traces connecting the terminals. There is also a risk of electrolysis and, because of the presence of salt (sodium chloride (NaCl)), the electrolysis reaction can mimic industrial processes for the production of chlorine and caustic soda (sodium hydroxide (NaOH)) production. The mixing of chlorine and sodium hydroxide in turn forms sodium hypochlorite (NaClO), the main ingredient of bleach. Thus, electrolysis at a two terminal electronic devices poses a potential risk of producing hazardous chemicals at a surface of the eye of a wearer.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and methods of forming a contact device or eye-mountable device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is a smart/eye contact device or contact device or eye-mountable device that includes circuitry that is formed in such a way to minimize or mitigate a potential risk of an electrolyte conversion of sodium chloride in tears (e.g., an oxidation of $Cl^-$ to $Cl_2$) and a conversion of water to hydroxide ion (a reduction of water) as well as the formation of sodium hypochlorite. Embodiments of an eye contact device or an eye-mountable device may include power supply circuitry, control electronics, accessory devices (e.g., an accommodation actuator), a sensor system (e.g., a capacitive sensor system), and an antenna all embedded within an enclosure material formed to be contact mounted to an eye. Because eye contact or eye mountable device 100 includes electronics and is configured to be contact mounted to an eye, the device is also referred to herein as an ophthalmic electronics platform, contact lens, or smart contact lens. In one embodiment, two terminal circuitry or devices (e.g., batteries, rectifiers, capacitors, resistors diodes) and traces connected to such two terminal devices include materials that minimize or mitigate the electrolysis of sodium chloride (NaCl) at a positive terminal (an anode) and/or water ($H_2O$) at a negative terminal (a cathode).

With regard to the components of an eye-mountable device or eye contact device, control electronics, in one embodiment, are representatively connected to monitor a sensor system to sense blood sugar levels of a wearer of the device. Information about blood sugar (glucose) levels is particularly useful for people with diabetes. The data related to blood sugar levels could be uploaded to a smartphone device and used by doctors and patients to monitor the data in almost real time. In another embodiment, control electronics are representatively connected to monitor a sensor system (e.g., a capacitive sensor system) to, for example, identify gaze direction/focal distance, manipulate an accessory device such as an accommodation actuator to control an optical power of the eye-mountable device, and provide wireless communications with an external reader. In some embodiments, a power supply may include charging circuitry for controlling inductive wireless charging of an embedded battery.

The enclosure material may be fabricated of a variety of materials compatible for direct contact with a human eye, such as a polymeric material, a hydrogel, PMMA, silicone based polymers (e.g., fluoro-silicon acrylate), or otherwise. The enclosure material can be in the form of a round lens with a concave curvature configured to mount to a corneal surface of an eye. The electronic components can be disposed upon a substrate embedded within the enclosure material near its periphery to avoid interference with incident light received closer to the central region of the cornea.

In an embodiment of a contact device that provides accommodation, gaze direction/focal distance information referenced above can be used to determine an amount of accommodation to be applied via a see-through accommodation actuator positioned in a central portion of the enclosure material. Such an accommodation actuator is connected to the controller to be electrically manipulated thereby. For example, an accommodation actuator maybe implemented with a liquid crystal cell that changes its index of refraction in response to an applied electrical bias signal. In other embodiments, the accommodation actuator may be implemented using other types of electro-active optical materials such as electro-optic materials that vary refractive index in the presence of an applied electric field or electro-mechanical structures that change the shape of a deformable lens.

Figure 1:
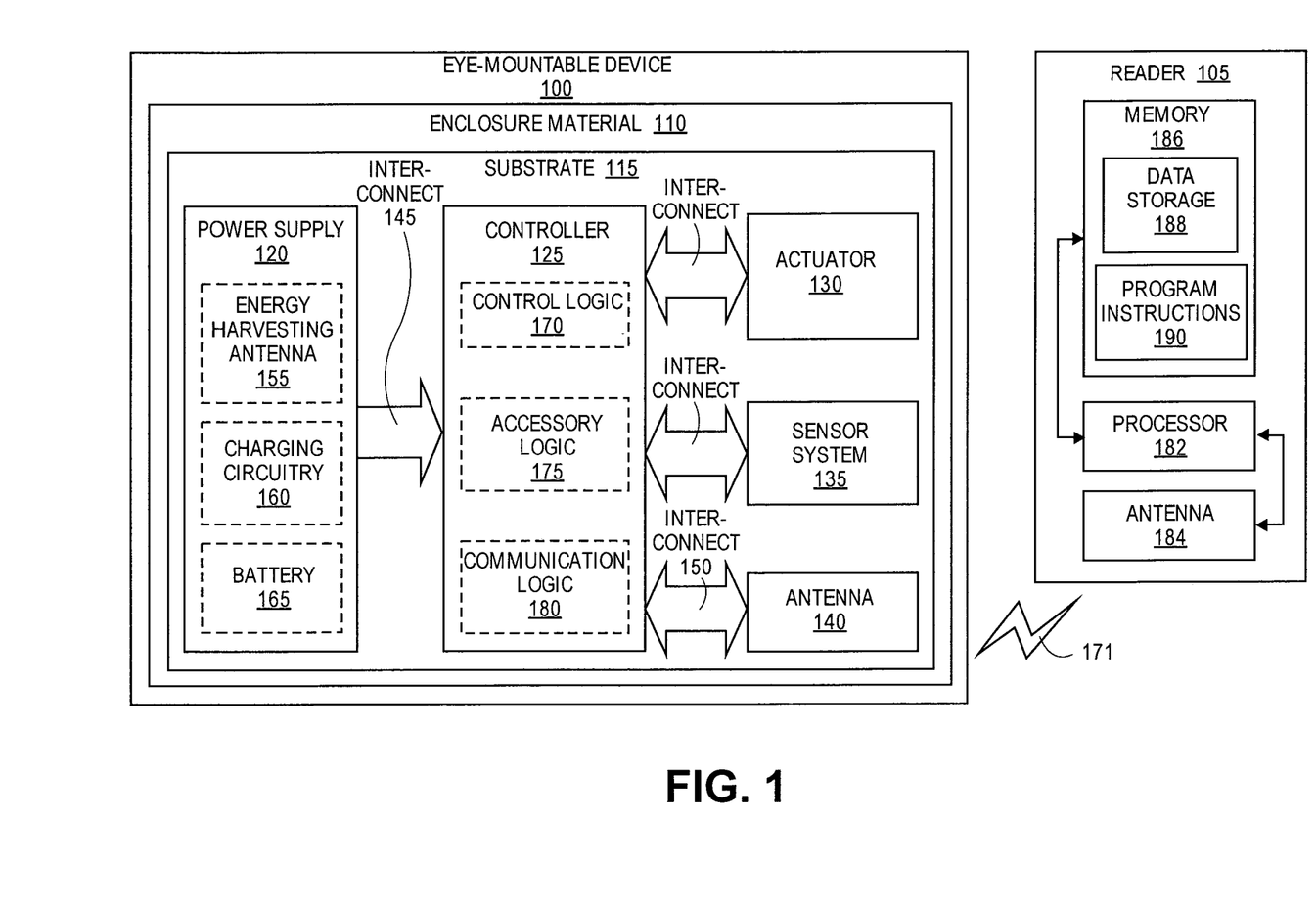
FIG. 1 is a functional block diagram of an eye-mountable device with capacitive gaze tracking for auto-accommodation along with an external reader, in accordance with an embodiment of the disclosure.

FIG. 1 is a functional block diagram of an eye-mountable device. In the illustrated embodiment, eye-mountable device 100 is associated with external reader 105, in accordance with an embodiment of the disclosure. The exposed portion of eye-mountable device 100 is enclosure material 110 formed to be contact-mounted to a corneal surface of an eye. Substrate 115 is embedded within or surrounded by enclosure material 110 to provide a mounting surface for power supply 120, controller 125, and representatively one or more accessory devices such as one or more actuators 130 (e.g., one or more accommodation actuators), and/or one or more sensor systems 135 (e.g., one or more capacitive sensor systems), antenna 140, and various interconnects 145 and 150. The illustrated embodiment of power supply 120 includes energy harvesting antenna 155, charging circuitry 160, and battery 165. The illustrated embodiment of controller 125 includes control logic 170, accessory logic 175 (e.g., accommodation logic), and communication logic 180. The illustrated embodiment of reader 105 includes processor 182, antenna 184, and memory 186. The illustrated embodiment of memory 186 includes data storage 188 and program instructions 190.

In an embodiment where eye mountable device 100 provides an accommodation feature, controller 125 is connected to receive feedback control signals from sensor system 135 (e.g., capacitive sensor system) and further connected to operate actuator 130 (an accommodation actuator). Power supply 120 supplies operating voltages to controller 125 and/or actuator 130. Antenna 140 is operated by the controller 125 to communicate information to and/or from eye-mountable device 100. In one embodiment, antenna 140, controller 125, power supply 120, and sensor system 135 are all situated on the embedded substrate 115. Because eye contact or eye mountable device 100 includes electronics and is configured to be contact mounted to an eye, the device is also referred to herein as an ophthalmic electronics platform, contact lens, or smart contact lens.

To facilitate contact-mounting, enclosure material 110 can have a concave surface configured to adhere ("mount") to a moistened corneal surface (e.g., by capillary forces with a tear film coating the corneal surface). Additionally or alternatively, eye-mountable device 100 can be adhered by a vacuum force between the corneal surface and enclosure material 110 due to the concave curvature. While mounted with the concave surface against the eye, the outward-facing surface of enclosure material 110 can have a convex curvature that is formed to not interfere with eye-lid motion while eye-mountable device 100 is mounted to the eye. For example, enclosure material 110 can be a substantially transparent curved disk shaped similarly to a contact lens.

Enclosure material 110 can include one or more biocompatible materials, such as those employed for use in contact lenses or other ophthalmic applications involving direct contact with the corneal surface. Enclosure material 110 can optionally be formed in part from such biocompatible materials or can include an outer coating with such biocompatible materials. Enclosure material 110 can include materials configured to moisturize the corneal surface, such as hydrogels and the like. In some instances, enclosure material 110 can be a deformable ("non-rigid") material to enhance wearer comfort. In some instances, enclosure material 110 can be shaped to provide a predetermined, vision-correcting optical power, such as can be provided by a contact lens. Enclosure material may be fabricated of various materials including a polymeric material, a hydrogel, PMMA, silicone based polymers (e.g., fluoro-silicon acrylate), or otherwise.

Substrate 115 includes one or more surfaces suitable for mounting devices thereon (e.g., devices including capacitive sensor system 135, controller 125, power supply 120, and antenna 140). Substrate 115 can be employed both as a mounting platform for chip-based circuitry (e.g., by flip-chip mounting) and/or as a platform for patterning conductive materials to create electrodes, interconnects, antennae, etc. In one embodiment, one or more devices or components on substrate 115 is a two terminal device or component (e.g., battery, rectifier, capacitor, diode, resistor, etc.) or is connected to a two terminal device by way of a conductive trace. Two terminal devices or components and traces connected thereto pose a possibility of electrolysis in the aqueous environment of the eye. In one embodiment, to minimize or mitigate a potential risk of an electrolytic conversion of sodium chloride present in tears (e.g., basal tears in humans) and water and to minimize or mitigate a formation of sodium hypochlorite, one or both terminals of a two terminal device and optionally traces connected thereto include materials that preferentially oxidize and are reduced at the positive terminal and negative terminal, respectively.

In one embodiment, a positive terminal of a two terminal device such as a battery or rectifier on substrate 115 includes a material having an electrode potential that is less than an electrode potential of chlorine. A reduction half reaction of chlorine has a standard reduction potential ($E^0$) of 1.36 volts and may be represented as follows:

$$Cl_2(g) + 2e^- \rightarrow 2Cl^-$$

One way to minimize or mitigate an oxidation of chloride ions in solution at a positive terminal to chlorine gas ($Cl_2(g)$) is to form the terminal of a material having a standard reduction potential that is less than the standard reduction potential of chlorine. Representative of such suitable materials are metal materials such as aluminum, zinc, iron and/or silver. The reduction half reactions of these representative metals and their standard reduction potentials are as follows:

$$Al^{3+} + 3e^- \rightarrow Al(s) \quad -1.66 \text{ V}$$

$$Zn^{2+} + 2e^- \rightarrow Zn(s) \quad -0.76 \text{ V}$$

$$Fe^{2+} + 2e^- \rightarrow Fe(s) \quad -0.44 \text{ V}$$

$$Ag^+ + e^- \rightarrow Ag(s) \quad 0.80 \text{ V}$$

By forming a positive terminal of a two terminal device and optionally any traces connecting to such positive terminal to include a metal having a standard reduction potential less than the standard reduction potential of chlorine, an oxidation of such metal to its ionic state (e.g., $Al^{3+}$, $Zn^{2+}$, $Ag^+$) at a positive electrode or anode will be favored over the oxidation of chloride ions (from sodium chloride) to chlorine gas. Representatively, an oxidation of silver metal ($Ag^0$) to silver ion ($Ag^+$) will be favored over an oxidation of chloride ion (Cl⁻) to chlorine gas (Cl₂), because of the difference in standard reduction potential (0.8 volts is less than 1.36 volts).

In addition or as an alternative to forming the positive terminal to include a material to minimize or mitigate the oxidation of chloride ion to form chlorine gas, in one embodiment, a negative terminal of a two terminal device may be formed to include a material to mitigate or minimize a production of hydrogen gas and sodium hydroxide. Representatively, the negative terminal, in one embodiment, includes a material having an electrode potential that favors reduction. Water (H₂O) as a standard reduction potential of −0.828 volts and the reduction half reaction may be represented as follows:

$$2H_2O + 2e^- \rightarrow H_2(g) + 2OH^-.$$

A material that has an electrode potential that favors reduction relative to water is a material that has a greater standard reduction potential. A suitable material is, for example, silver chloride (AgCl) with a standard reduction potential of 0.22 volts (0.22 volts is greater than −0.828 volts). The reduction half reaction of silver chloride may be represented as follows:

$$AgCl + e^- \rightarrow Ag(s) + Cl^-.$$

By forming the negative terminal to include a material that favors reduction relative to water, a material such as silver chloride can intercept the electrons produced at the negative terminal (cathode) and such silver chloride would be reduced to silver metal (Ag(s)) and chloride ion (Cl⁻). It is appreciated that for a terminal of a two terminal device, the terminal should include a conductive material. Thus, where a material selected for its property to be reduced relative to water is not conductive, a conductive material can be combined with such material. Thus, in one embodiment, where the material having an electrode potential that favors reduction relative to water is silver chloride (generally non-conductive), such material may be mixed with an amount of silver metal (conductive). In another embodiment, both the positive electrode and the negative electrode and optionally traces connected to either of the electrode includes a mixture of silver and silver chloride.

In one embodiment, an eye contact device or eye mountable device includes at least one of a positive terminal including a first material having a standard reduction potential that is less than a standard reduction potential of chlorine, and a negative terminal including a second material having an electrode potential that favors reduction relative to a reduction of water. In another embodiment, an eye contact device or eye mountable device includes each of a positive terminal including a first material having a standard reduction potential that is less than a standard reduction potential of chlorine, and a negative terminal including a second material having an electrode potential that favors reduction relative to a reduction of water.

In another embodiment, a method of forming a positive terminal and/or a negative terminal of a two terminal device is disclosed. The method includes at least one of forming a positive terminal of a two terminal device in an eye contact device, the positive terminal including a first material having a standard reduction potential that is less than a standard reduction potential of chlorine; and forming a negative terminal of the two terminal device including a second material having an electrode potential that favors reduction relative to a reduction of water. One way the materials of a positive terminal and/or negative terminal may be formed is by screen-printing. Thus, screen-printing onto substrate 115 is to form a circuitry, terminals for a battery or rectifier, electrodes, etc. For example, an antenna and other traces are formed of a combination of silver and silver chloride (Ag/AgCl) that can be printed using screen-printing techniques on substrate 115. In another embodiment, the suitable materials may be formed by depositing such materials on the substrate (e.g., chemical vapor deposition). A combination of resist, mask and deposition technique can be employed to pattern materials on substrate 115.

Substrate 115 can be a relatively rigid material, such as polyethylene terephthalate ("PET") or another material sufficient to structurally support the circuitry and/or electronics within enclosure material 110. Eye-mountable device 100 can alternatively be arranged with a group of unconnected substrates rather than a single substrate. For example, controller 125 and power supply 120 can be mounted to one substrate, while antenna 140 and sensor system 135 are mounted to another substrate and the two can be electrically connected via interconnects.

In some embodiments, power supply 120 and controller 125 (and the substrate 115) can be positioned away from the center of eye-mountable device 100 and thereby avoid interference with light transmission to the eye through the center of eye-mountable device 110. In contrast, actuator 130 can be centrally positioned to apply optical accommodation to the light transmitted to the eye through the center of eye-mountable device 110. For example, where eye-mountable device 100 is shaped as a concave-curved disk, substrate 115 can be embedded around the periphery (e.g., near the outer circumference) of the disk.

Substrate 115 can be shaped as a flattened ring with a radial width dimension sufficient to provide a mounting platform for the embedded electronics components. Substrate 115 can have a thickness sufficiently small to allow the substrate to be embedded in enclosure material 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes battery 165 to power the various embedded electronics, including controller 125. Battery 165 having a positive electrode and/or a negative electrode as described above may be inductively charged by charging circuitry 160 and energy harvesting antenna 155 which itself may include a positive electrode and/or a negative electrode as described above. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time-shared for their respective functions of inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accessory logic 175 includes logic for monitoring and/or directing an operation of one or more accessory devices. Representatively, where eye-contact or eye-mountable device 110 is configured for accommodation or to adjust a focus, accessory logic 175 includes accommodation logic for monitoring feedback signals from, for example, sensor system 135 (e.g., a capacitive sensor system), determining the current gaze direction or focal distance of the user, and manipulating actuator 130 in response to provide the appropriate accommodation. The auto-accommodation can be implemented in real-time based upon feedback from the capacitive gaze tracking, or permit user control to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

It is noted that the block diagram shown in FIG. 1 is described in connection with functional modules for convenience in description, but does not necessarily connote physical organization. Rather, embodiments of eye-mountable device 100 can be arranged with one or more of the functional modules ("sub-systems") implemented in a single chip, multiple chips, in one or more integrated circuits, or otherwise.

External reader 105 includes antenna 184 (or group of more than one antennae) to send and receive wireless communication link 171 to and from eye-mountable device 100. In one embodiment, external reader 105 also includes a computing system with processor 182 in communication with memory 186. Memory 186 is a non-transitory computer-readable medium that can include, without limitation, magnetic disks, optical disks, organic memory, and/or any other volatile (e.g. RAM) or non-volatile (e.g. ROM) storage system readable by processor 182. Memory 186 can include data storage 188 to store indications of data, such as data logs (e.g., user logs), program settings (e.g., to adjust behavior of eye-mountable device 100 and/or external reader 105), etc. Memory 186 can also include program instructions 190 for execution by processor 182 to cause external reader 105 to perform processes specified by the instructions 190. For example, program instructions 190 can cause external reader 105 to provide a user interface that allows for retrieving information communicated from eye-mountable device 100 or allows transmitting information to eye-mountable device 100 to program or otherwise select operational modes of eye-mountable device 100. External reader 105 can also include one or more hardware components for operating antenna 184 to send and receive wireless communication link 171 to and from eye-mountable device 100.

External reader 105 can be a smart phone, digital assistant, or other portable computing device with wireless connectivity sufficient to provide wireless communication link 171. External reader 105 can also be implemented as an antenna module that can be plugged in to a portable computing device, such as in an example where wireless communication link 171 operates at carrier frequencies not commonly employed in portable computing devices. In some instances, external reader 105 is a special-purpose device configured to be worn relatively near a wearer's eye to allow wireless communication link 171 to operate with a low power budget. For example, external reader 105 can be integrated in a piece of jewelry such as a necklace, earring, etc. or integrated in an article of clothing worn near the head, such as a hat, headband, etc.

Figure 2A:
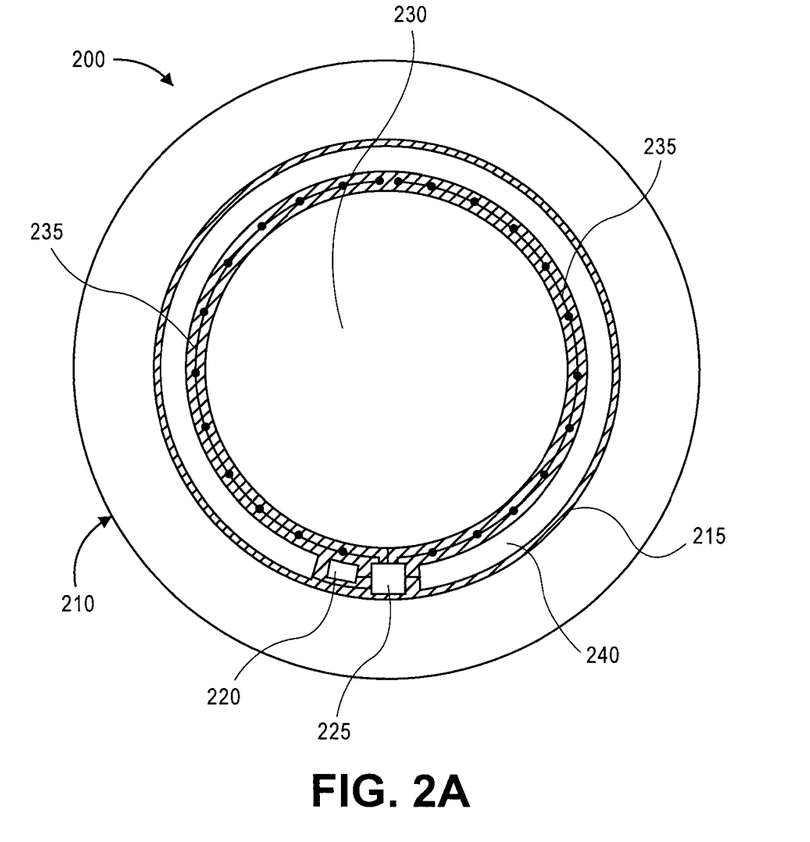
FIG. 2A is a top view of an eye-mountable device, in accordance with an embodiment of the disclosure.
Figure 2B:
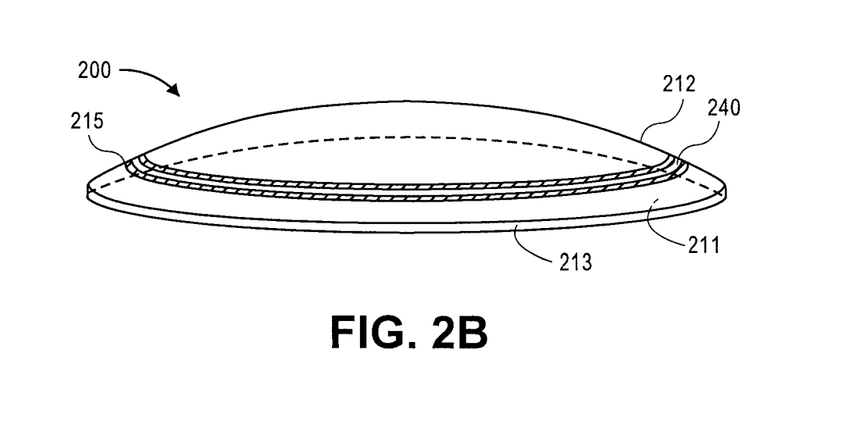
FIG. 2B is a perspective view of an eye-mountable device, in accordance with an embodiment of the disclosure.

FIGS. 2A and 2B illustrate two views of eye-mountable device 200, in accordance with an embodiment of the disclosure. FIG. 2A is a top view of eye-mountable device 200 while FIG. 2B is a perspective view of the same. Eye-mountable device 200 is one possible implementation of eye-mountable device 100 illustrated in FIG. 1. The illustrated embodiment of eye-mountable device 200 includes enclosure material 210, substrate 215, a power supply 220, controller 225, accommodation actuator 230, capacitive sensor system 235, and antenna 240. It should be appreciated that FIGS. 2A and 2B are not necessarily drawn to scale, but have been illustrated for purposes of explanation only in describing the arrangement of the example eye-mountable device 200.

Enclosure material 210 of eye-mountable device 200 is shaped as a curved disk. Enclosure material 210 is a substantially transparent material to allow incident light to be transmitted to the eye while eye-mountable device 200 is mounted to the eye. Enclosure material 210 is a biocompatible material similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Enclosure material 210 can be formed with one side having concave surface 211 suitable to fit over a corneal surface of an eye. The opposite side of the disk can have convex surface 212 that does not interfere with eyelid motion while eye-mountable device 200 is mounted to the eye. In the illustrated embodiment, a circular or oval outer side edge 213 connects concave surface 211 and convex surface 212.

In one embodiment, eye-mountable device 200 has dimensions similar to a vision correction and/or cosmetic (contact lens), such as a diameter of approximately one centimeter, and a thickness of about 0.1 to about 0.5 millimeters. In some embodiments, the dimensions of eye-mountable device 200 are selected according to the size and/or shape of the corneal surface of an eye of a wearer. Enclosure material 210 can be formed with a curved shape in a variety of ways. For example, techniques similar to those employed to form vision-correction contact lenses, such as heat molding, injection molding, spin casting, etc. can be employed to form enclosure material 210.

Substrate 215 is embedded within enclosure material 210. Substrate 215 can be embedded to be situated along the outer periphery of enclosure material 210, away from the central region where accommodation actuator 230 is positioned. In the illustrated embodiment, substrate 215 encircles accommodation actuator 230. Substrate 215 does not interfere with vision because it is too close to the eye to be in focus and is positioned away from the central region where incident light is transmitted to the light-sensing portions of the eye. In some embodiments, substrate 215 can optionally be formed of a transparent material to further mitigate effects on visual perception. Substrate 215 can be shaped as a flat, circular ring (e.g., a disk with a centered hole). The flat surface of substrate 215 (e.g., along the radial width) is a platform for mounting electronics and for patterning conductive materials to form electrodes, antenna(e), and/or interconnections.

Figure 3A:
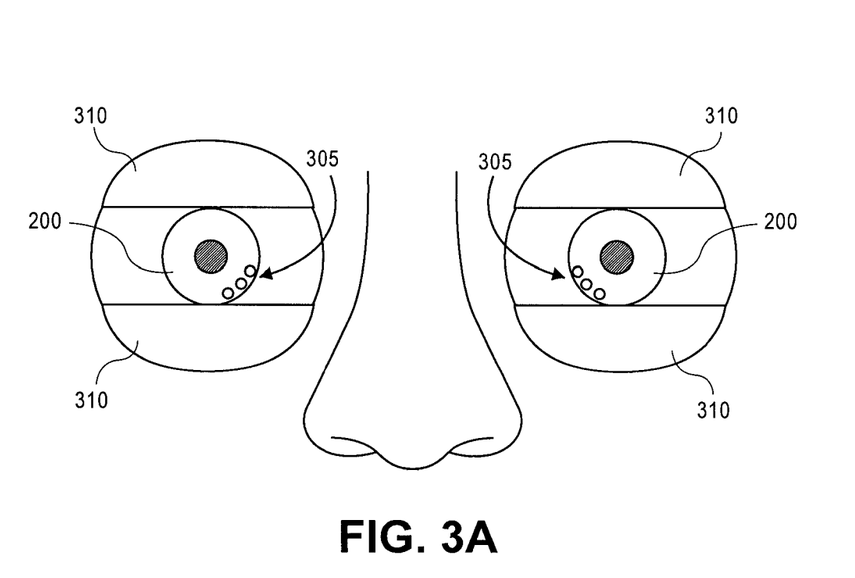
FIGS. 3A-3B illustrate the general operation of a capacitive gaze detection mechanism, in accordance with an embodiment of the disclosure.
Figure 3B:
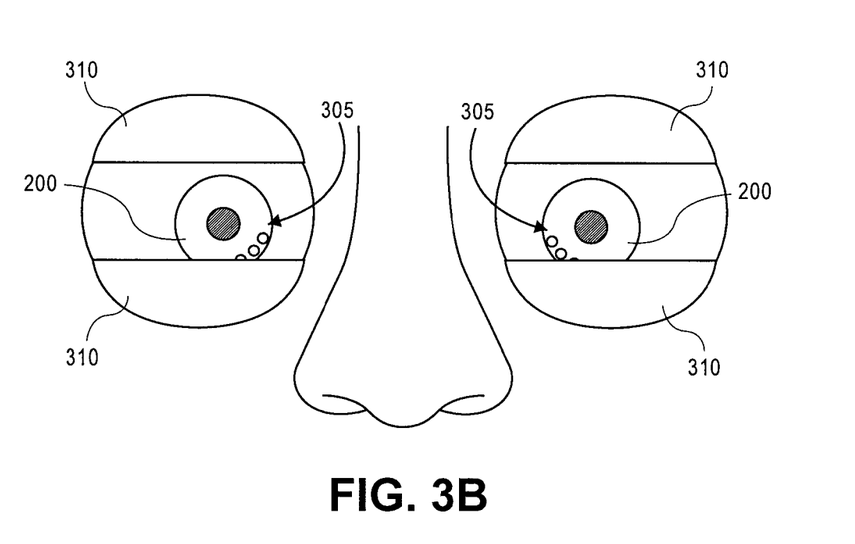

In one embodiment, capacitive sensor system 235 is distributed about eye-mountable device 200 to sense eyelid overlap in a manner similar to capacitive touch screens. By monitoring the amount and position of eyelid overlap, feedback signals from capacitive sensor system 235 can be measured by controller 225 to determine the approximate gaze direction and/or focal distance. Referring to FIG. 3A, eye-mountable device 200 is disposed on a cornea that is looking straight forward. In this position, capacitance sensors 305 are not overlapped by eyelids 310, which influences their capacitance value. Controller 225 (see FIG. 2A) can determine that the cornea is looking straight forward via the feedback signals from capacitance sensors 305. In this scenario, controller 225 may determine that the user is focusing on the far-field and the accommodation adjusted accordingly. Correspondingly, as illustrated in FIG. 3B, if controller 225 determines, based upon the amount and locations of eyelid 310 overlap of capacitance sensors 305, that the cornea is looking down and inward towards the nose, then it can be assumed the user is focusing on the near-field (e.g., reading). In this scenario, the amount of accommodation applied by accommodation actuator 230 should correspond to a near-field focal distance associated with the activity of reading.

Capacitive sensor system 235 is disposed within enclosure material 210 on substrate 215. In the illustrated embodiment, capacitive sensor system 235 is distributed peripherally around accommodation actuator 230. In the illustrated embodiment, capacitive sensor system 235 is disposed along the inner edge of substrate 215 between antenna 240 and accommodation actuator 230. In other embodiments, capacitive sensor system 235 may be partially or entirely distributed along the outer edge of substrate 215 peripherally to antenna 240. Capacitive sensor system 235 may be disposed on a backside of substrate 215 adjacent to concave surface 211 or on the front side of substrate 215 adjacent to convex surface 212. Several orientations, groupings, and distributions may be used to implement capacitive sensor system 235. In the illustrated embodiment, capacitive sensor system 235 includes a plurality of discrete capacitance sensors coupled to a common read-line; however, various implementations include a single elongated capacitance sensor, a plurality of discrete capacitance sensors, multiple discrete capacitance sensors coupled in parallel via a common read-line, multiple independent branches of parallel coupled discrete capacitance sensors, etc.

Returning to FIG. 2A, loop antenna 240 is a layer of conductive material patterned (e.g., screen printed) along the flat surface of the substrate to form a flat conductive ring. In some examples, to allow additional flexibility along the curvature of the enclosure material, loop antenna 240 can include multiple substantially concentric sections electrically joined together. Each section can then flex independently along the concave/convex curvature of eye-mountable device 200. In some examples, loop antenna 240 can be formed without making a complete loop. For instances, antenna 240 can have a cutout to allow room for controller 225 and power supply 220, as illustrated in FIG. 2A. However, loop antenna 240 can also be arranged as a continuous strip of conductive material that wraps entirely around the flat surface of substrate 215 one or more times. For example, a strip of conductive material with multiple windings can be patterned on the backside of substrate 215 opposite controller 225, power supply 220, and capacitive sensor system 235. Interconnects between the ends of such a wound antenna (e.g., the antenna leads) can then be passed through substrate 215 to controller 225.

FIGS. 4A-4E illustrate different capacitance sensor layouts for implementing a capacitive sensor system of an eye-mountable device, in accordance with various embodiments of the disclosure. These capacitive sensor systems represent possible implementations of capacitive sensor systems 135 or 235 as illustrated in FIG. 1 and FIG. 2A.

Figure 4A:
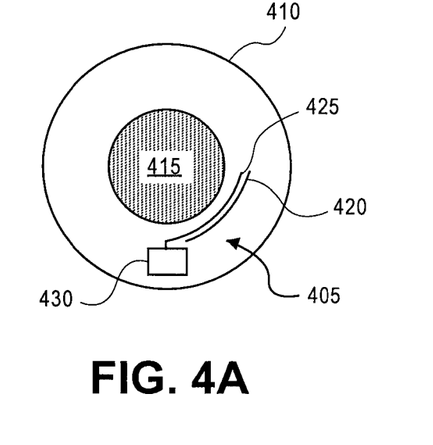
FIGS. 4A-4E illustrate different capacitance sensor layouts on an eye-mountable device for a capacitive sensor system, in accordance with embodiments of the disclosure.

FIG. 4A illustrates a capacitive sensor system 405 disposed within an eye-mountable device 410. Capacitive sensor system 405 is a single elongated capacitor that partially encircles accommodation actuator 415. Capacitive sensor system 405 includes a ground electrode 420 and a read-line 425 that is coupled to a controller 430. When the cornea moves, eyelids overlap the elongated capacitor causing its capacitance value to change as a continuously changing analog value. Different capacitance values can be associated with different gazing directions or focal distances and thereby used to determine a user's gazing direction or focal distance.

In some embodiments, the separation distance between read-line 425 and ground electrode 420 is constant. In other embodiments, the separation distance between read-line 425 and ground electrode 420 varies with position. By using a variable separation distance, the linear capacitance of the capacitor changes along its length. This changing linear capacitance results in different capacitance changes when overlapped by an eyelid at different locations along its length. This variable linear capacitance provides improved differentiation for determining both position and amount of eyelid overlap and therefore improved capacitive gaze tracking.

Figure 4B:
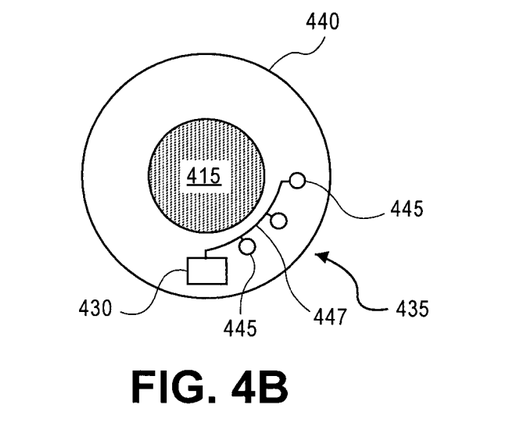

FIG. 4B illustrates capacitive sensor system 435 disposed within eye-mountable device 440. Capacitive sensor system 435 includes a plurality of discrete capacitance sensors 445 coupled in parallel between a common ground (not illustrated) and a common read-line 447. Each discrete capacitance sensor 445 may have the same capacitance value or a different capacitance value. When the cornea moves, eyelids overlap the various discrete capacitance sensors 445 causing the total capacitance value on read-line 447 to change. Different capacitance values can be associated with different gazing directions or focal distances and thereby used to determine a gazing direction of a user or a focal distance. By selecting each capacitance sensor 445 to have a different capacitance value, controller 430 has improved differentiation to determine which capacitance sensor 445 has been overlapped by an eyelid. The capacitance values of the different sized capacitance sensors 445 will change by different amounts when overlaid. Capacitive sensor system 435 does not entirely encircle accommodation actuator 415. Rather, in the illustrated embodiment, capacitive sensor system 435 is located in a lower quadrant closest to a user's nose for a rotationally stable contact lens. It is anticipated that this quadrant will provide increased sensitivity for distinguishing near-field activities since eyes move down and inward when reading. In one embodiment, the lower, inner quadrant is populated with a higher density of capacitance sensor than the other quadrants for increased sensitivity in this region.

Figure 4C:
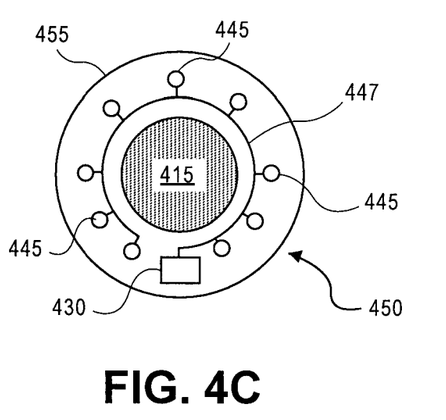

FIG. 4C illustrates capacitive sensor system 450 disposed within eye-mountable device 455. Capacitive sensor system 450 is similar to capacitive sensor system 435 illustrated in FIG. 4B, but includes a greater number of discrete capacitance sensors 445 more fully encircling accommodation actuator 415. Capacitive sensor system 450 is well suited for non-rotationally stable contact lens embodiments since it cannot be anticipated which quadrant of eye-mountable device 455 will end up being the lower inward quadrant closest to the user's nose.

Figure 4D:
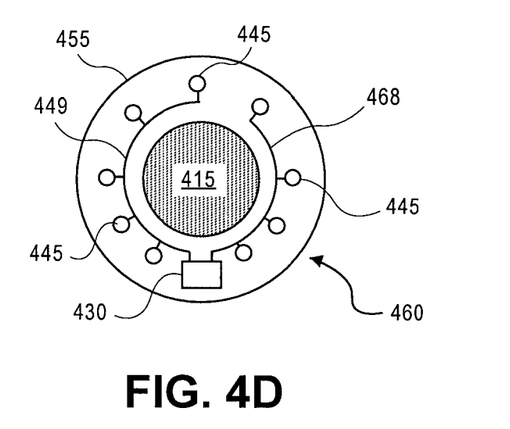

FIG. 4D illustrates capacitive sensor system 460 disposed within eye-mountable device 465. Capacitive sensor system 460 includes multiple branches 448 and 449 of parallel coupled discrete capacitance sensors 445. Each branch 448 or 449 has an independent read-line connection to controller 430. In one embodiment, the multiple branches share a common ground (not illustrated). Capacitance sensors 445 may each have the same or different capacitance values. Increasing the number of independent read-line branches provides greater differentiation to disambiguate between scenarios that cause similar changes in capacitance values thereby improving gaze direction sensing. However, this should be balanced with the cost and complexity associated with increased inputs on controller 430 and trace lines. Although FIG. 4D illustrates just two independent branches 448 and 449, it should be appreciated that more than two independent branches may be implemented.

Figure 4E:
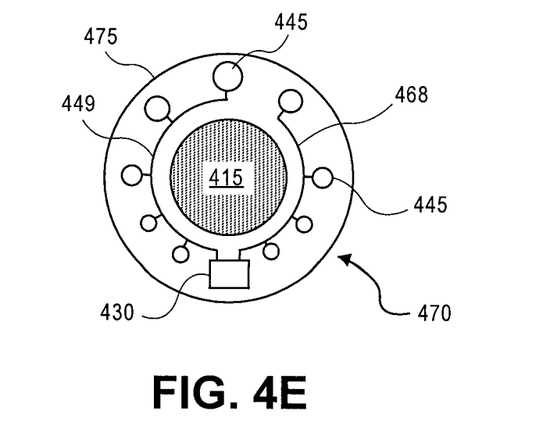

FIG. 4E illustrates capacitive sensor system 470 disposed within eye-mountable device 465. Capacitive sensor system 470 includes multiple branches 448 and 449 of parallel coupled discrete capacitance sensors 445. Capacitive sensor system 470 is similar to capacitive sensor system 460, except that the capacitance values of each discrete capacitance sensor 445 vary in sensitivity (capacitance) in opposite directions around the perimeter of eye-mountable device 475. This configuration is anticipated to discriminate absolute rotational position as well as eyelid coverage.

It should be appreciated that the embodiments illustrated in FIGS. 4A-4E may be combined into hybrid embodiments. For example, in one hybrid embodiment (combination of FIG. 4A and FIG. 4E), two independent elongated capacitors may be used, which vary in amount of separation between their respective electrodes, but vary in opposite directions along their lengths. This may be used to provide both eyelid position information and information about the amount of eyelid coverage. For example, a first capacitor 1 separation distance between its electrodes may vary with $E1(x)=A*x$, and second capacitor 2 separation distance between its electrodes may vary with $E2(x)=A*(L-x)$, where L is the length of the electrode, A is the rate of scaling, and $E1(x)$ and $E2(x)$ are the amount of electrode separation. In this example, the distance is linearly scaled. However, distance may instead be scaled in a non-linear ways to provide linearly or non-linearly changing capacitance changes relative to eyelid coverage/position.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

While certain embodiments and examples describe above relate to an eye contact device include gaze accommodation related sensors and other circuitry, it is appreciated that the teachings herein with respect to circuitry operable to or formed in such a way to minimize our mitigate a potential risk of a potentially hazardous electrolyte conversion are suitable in other eye contact devices included, for example, eye contact devices associated with blood sugar (glucose) sensing, or blood sugar sensing and monitoring.

The above description of illustrated embodiments, including what is described in the Abstract, is not intended to be exhaustive or to limit the claims to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye contact device comprising:
   a battery including a positive terminal and a negative terminal;
   an enclosure material having the battery disposed therein, wherein the enclosure material is configured to prevent solution ingression into the eye contact device at the positive terminal and the negative terminal, wherein the positive terminal comprises a first material having a standard reduction potential that is less than a standard reduction potential of chlorine, and the negative terminal comprises a second material having an electrode potential that favors reduction relative to a reduction of water, wherein the second material of the negative terminal comprises a combination of silver chloride and silver metal;
   an accommodation actuator disposed within the enclosure to provide variable optical power;

a controller disposed within the enclosure material and coupled to the positive and negative terminals of the battery and to the accommodation actuator; and interconnection traces disposed within the enclosure and linking the controller to the battery or the controller to the accommodation actuator, wherein the interconnection traces each comprise the combination of silver chloride and silver metal.

2. The eye contact device of claim 1, wherein the first material comprises the combination of silver chloride and silver metal.

3. The eye contact device of claim 1, further comprising a rectifier, wherein the rectifier includes a positive terminal formed from the first material and a negative terminal formed from the second material.

4. The eye contact device of claim 1, wherein each of the positive terminal and the negative terminal comprise a combination of silver and silver chloride.

5. The eye contact device of claim 1, wherein the first material and the second material prevent the formation of at least one of NaClO, Cl, or NaOH when the solution ingresses into the eye contact device.

6. A method comprising one of:
forming a positive terminal of a battery in an eye contact device, the positive terminal comprising a first material having a standard reduction potential that is less than a standard reduction potential of chlorine;

forming a negative terminal of the battery comprising a second material having an electrode potential that favors reduction relative to a reduction of water, wherein the second material of the negative terminal comprises a combination of silver chloride and silver metal;

forming first interconnection traces extending between the positive and negative terminals of the battery and a controller;

forming a second interconnection trace extending between the controller and an accommodation actuator that provides variable optical power; and forming an enclosure material around the battery, the controller, the accommodation actuator, the first interconnection traces, and the second interconnection trace to prevent solution ingression into the eye contact device at the positive terminal, the negative terminal, the first interconnection traces, or the second interconnection trace, wherein the first interconnection traces and the second interconnection trace each comprise the combination of silver chloride and silver metal.

7. The method of claim 6, wherein forming the positive terminal comprises forming one or more traces coupled thereto.

8. The method of claim 6, wherein forming the negative terminal comprises forming one or more traces coupled thereto.

9. The method of claim 6, wherein forming the positive terminal and forming the negative terminal comprise printing the first material and the second material.

10. The method of claim 6, wherein the first material is selected from the group consisting of silver, zinc, iron and aluminum.

11. The method of claim 10, wherein the first material comprises silver.

12. The method of claim 6, wherein each of the positive terminal and the negative terminal comprise a combination of the first material and the second material.

13. An ophthalmic device comprising:
an enclosure; and
a battery disposed in the enclosure, the battery including first and second terminals formed from a combination of silver and silver chloride, wherein the enclosure is configured to prevent solution ingression into the ophthalmic device at the first and second terminals which are surrounded by the enclosure;

control electronics disposed in the enclosure and electrically coupled to the battery via one or more first traces formed from the combination of silver and silver chloride; and an accommodation actuator disposed in the enclosure and electrically coupled to the control electronics via one or more second traces formed from the combination of silver and silver chloride.

14. The ophthalmic device of claim 13, further comprising:
a power supply disposed in the enclosure, wherein the power supply includes the battery, and further includes:
charging circuitry coupled to regulate inductive charging of the battery; and
an energy harvesting antenna coupled to the charging circuitry to facilitate the inductive charging.

15. The ophthalmic device of claim 14, wherein the charging circuitry includes an energy storage device coupled to mitigate high frequency variations in energy provided by the energy harvesting antenna, and
wherein the energy harvesting antenna includes positive and negative electrodes formed from the combination of silver and silver chloride.

16. The ophthalmic device of claim 15, wherein the energy storage device is a capacitor or an inductor.

17. The ophthalmic device of claim 13, further comprising:
a sensor system disposed in the enclosure and coupled to the control electronics, the sensor system coupled to provide a feedback signal to the control electronics.

18. The ophthalmic device of claim 13, further including:
an antenna disposed in the enclosure and electrically coupled to the control electronics, the antenna coupled for wireless communications with an external reader.

19. An eye contact device comprising:
a battery including a positive terminal and a negative terminal;
an enclosure material having the battery disposed therein, wherein the enclosure material is configured to prevent solution ingression into the eye contact device at the positive terminal and the negative terminal, wherein the positive terminal comprises a first material having a standard reduction potential that is less than a standard reduction potential of chlorine, and the negative terminal comprises a second material having an electrode potential that favors reduction relative to a reduction of water, wherein the first and second materials comprise a combination of silver chloride and silver metal;
a rectifier disposed within the enclosure material and coupled to the positive and negative terminals via first interconnection traces formed from the combination of silver chloride and silver metal; and
a controller disposed within the enclosure material and coupled to the positive and negative terminals of the battery via second interconnection traces also formed from the combination of silver chloride and silver metal.

* * * * *